United States Patent
Guo et al.

(10) Patent No.: US 12,152,025 B2
(45) Date of Patent: Nov. 26, 2024

(54) PROCESS FOR PREPARING ALKYNYL-CONTAINING COMPOUND AND INTERMEDIATE THEREOF

(71) Applicants: Ascentage Pharma (Suzhou) Co., Ltd., Jiangsu (CN); Ascentage Pharma Group Corp Limited, Hong Kong (CN); GUANGZHOU HEALTHQUEST PHARMA CO., LTD., Guangdong (CN)

(72) Inventors: Ming Guo, Suzhou (CN); Jianfeng Wen, Suzhou (CN); Shangjun Teng, Suzhou (CN); Tianzhu Wu, Suzhou (CN); Jianpeng Feng, Suzhou (CN)

(73) Assignees: Ascentage Pharma (Suzhou) Co., Ltd., Jiangsu (CN); Ascentage Pharma Goup Corp Limited, Hong Kong (CN); GUANGZHOU HEALTHQUEST PHARMA CO., LTD., Guangdong (CN)

( * ) Notice: Subject to any disclaimer, the term of this patent is extended or adjusted under 35 U.S.C. 154(b) by 878 days.

(21) Appl. No.: 17/264,762

(22) PCT Filed: Feb. 26, 2020

(86) PCT No.: PCT/CN2020/076728
§ 371 (c)(1),
(2) Date: Jan. 29, 2021

(87) PCT Pub. No.: WO2021/164045
PCT Pub. Date: Aug. 26, 2021

(65) Prior Publication Data
US 2022/0112186 A1   Apr. 14, 2022

(30) Foreign Application Priority Data
Feb. 21, 2020 (CN) .......................... 202010108764.8

(51) Int. Cl.
*C07D 471/04* (2006.01)
(52) U.S. Cl.
CPC .................................. *C07D 471/04* (2013.01)
(58) Field of Classification Search
CPC ..................................................... C07D 471/04
USPC .......................................................... 544/362
See application file for complete search history.

(56) References Cited

FOREIGN PATENT DOCUMENTS

| CN | 103214480 A | 7/2013 |
|---|---|---|
| CN | 106632347 A | 5/2017 |
| EP | 2594567 A1 | 5/2013 |
| WO | WO 2012/000304 A1 | 1/2012 |
| WO | WO 2015/108490 A2 | 7/2015 |

*Primary Examiner* — Taylor V Oh
(74) *Attorney, Agent, or Firm* — Jones Day

(57) ABSTRACT

Disclosed herein are a process for preparing alkynyl-containing compound and intermediate thereof. In particular, the present invention discloses a process for preparing a compound of formula 6 as shown in below and a pharmaceutical composition comprising a compound of formula 6 for treating cancer,

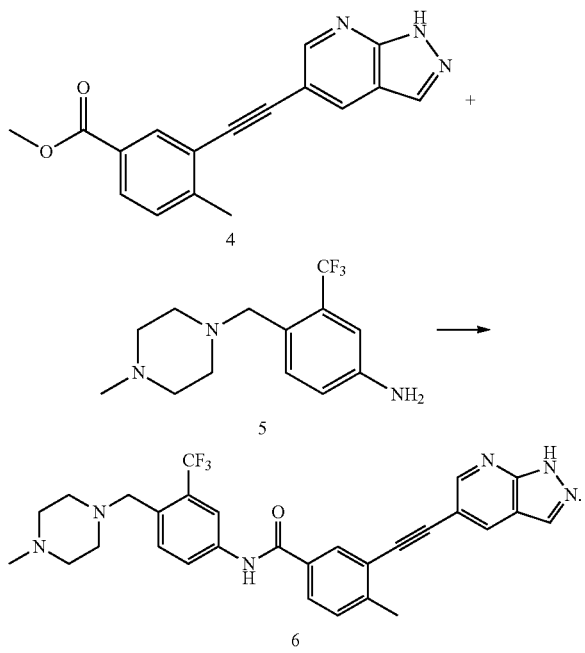

19 Claims, No Drawings

PROCESS FOR PREPARING ALKYNYL-CONTAINING COMPOUND AND INTERMEDIATE THEREOF

The present application is a national phase entry pursuant to 35 U.S.C. § 371 of International Application No. PCT/CN2020/076728, filed on Feb. 26, 2020, which claims the priority of the Chinese patent application No. CN202010108764.8, filed on Feb. 21, 2020, the contents of all of which are incorporated herein by reference in their entireties.

FIELD OF THE INVENTION

The present invention relates to a method for preparing compounds that contain an alkynyl moiety and a method of use thereof for treating cancer.

BACKGROUND OF THE INVENTION

Cancer has a major impact on society across the world. Cancer is the second most common cause after cardiovascular disease responsible for human death. The National Cancer Institute estimates that in 2015, approximately 1,658,370 new cases of cancer will be diagnosed in the United States and 589,430 people will die from the disease.

Chronic myeloid leukemia (CML) is a type of cancer that starts in certain blood forming cells of the bone marrow. CML cells contain an abnormal gene, BCR-ABL, causes CML cells to grow and reproduce out of control. BCR-ABL is a type of protein known as a tyrosine kinase. Drugs known as tyrosine kinase inhibitors (TKIs) that target BCR-ABL are the standard treatment for CML.

Imatinib (Gleevec®) is the first drug to specifically target the BCR-ABL tyrosine kinase protein for treating CML. However, emerging acquired resistance to imatinib has become a major challenge for clinical management of CML. More than 100 resistance-related BCR-ABL mutants have been identified in the clinic, among which the "gatekeeper" T315I is most common mutation, as it accounts for approximately 15-20% of all clinically acquired mutants. Ren et al., J. Med Chem. 2013, 56, 879-894.

Great efforts have been devoted to identifying new BCR-ABL inhibitors to overcome imatinib resistance. GZD824 is a novel oral bioavailable Bcr-Abl inhibitor that is effective against broad-spectrum expression of drug mutants including T315I. GZD824 and its preparation are described in PCT publication, WO2012/000304. However, the method of preparing GZD824 disclosed in WO2012/000304 involves multiple synthetic steps, wide variety of chemical reagents, harsh reaction conditions including the use of pressure-resistant sealed tubes, high reaction temperature, and high performance liquid chromatography for purification at each synthetic step. Thus, the known method limits the large scale production.

Accordingly, there is a need for an efficient and cost effective route to prepare GZD824. The present invention provides a novel method for product GZD824, which uses mild reaction conditions and is capable of achieving higher yields for large-scale industrial production.

SUMMARY OF THE INVENTION

In certain embodiments, provided herein is a method for preparing GZD824 (Compound 6) that has the following structure:

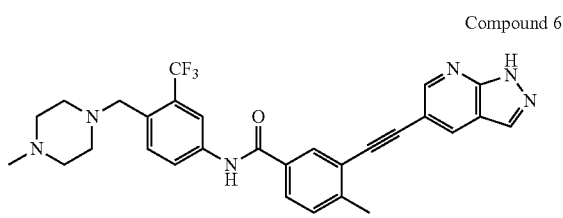 [SMILES: Cc1ccc(C(=O)Nc2ccc(CN3CCN(C)CC3)c(C(F)(F)F)c2)cc1C#Cc1cnc2[nH]ncc2c1]

Compound 6 wherein, the method comprises reacting a compound of formula 4 and a compound of formula 5 to provide Compound 6 or a pharmaceutically acceptable salt as shown in I below:

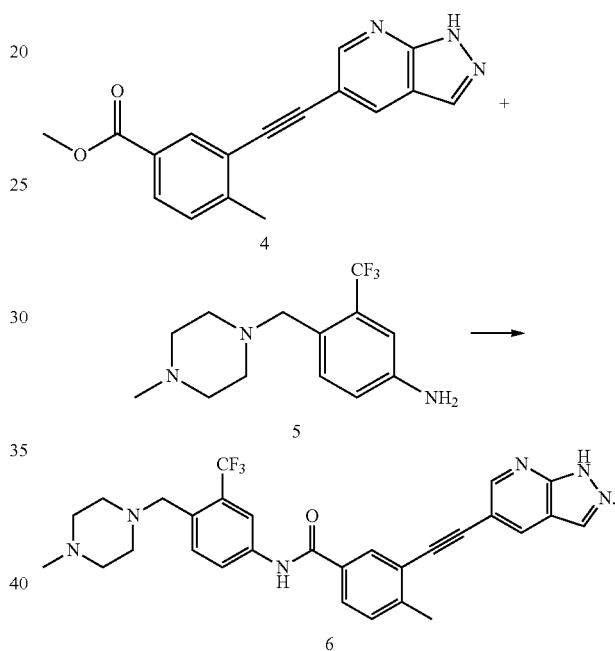

Scheme I

In some embodiments, the method described in Scheme I is a amidation reaction, which is carried out under the protection of nitrogen or inert gas;

and/or, in the amidation reaction, the solvent comprises ether solvents, DMF, N,N-dimethylacetamide, DMSO, N-methylpyrrolidone, toluene or acetonitrile;

and/or, in the amidation reaction, the volume/mass ratio of the solvent to the compound of formula 4 is (about 5 to about 17) mL:1 g;

and/or, in the amidation reaction, the base is an organic base and/or an inorganic base;

and/or, in the amidation reaction, the molar ratio of the base to the compound of formula 4 is (about 1.5 to about 10):1;

and/or, in the amidation reaction, the base is added to the mixture composed of the rest materials in batches;

and/or, in the amidation reaction, the molar ratio of the compound of formula 5 to the compound of formula 4 is (about 0.8 to about 1.5):1;

and/or, in the amidation reaction, the reaction temperature of the amidation reaction is within a range from about −80° C. to about 10° C.;

and/or, in the amidation reaction, optionally the post-treatment of the amidation reaction comprises washing the reaction solution with water and/or brine.

DETAILED DESCRIPTION OF THE INVENTION

Unless defined otherwise, all technical and scientific terms used herein have the same meaning as commonly understood by one of ordinary skill in the art to which this disclosure belongs.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "comprises" refers to "includes, but is not limited to."

As used herein, the terms "treatment," "treat," and "treating" refer to reversing, alleviating, delaying the onset of, or inhibiting the progress of a disease or disorder, or one or more symptoms thereof, including but not limited to therapeutic benefit. In some embodiments, treatment is administered after one or more symptoms have developed. In some embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

Therapeutic benefit includes eradication and/or amelioration of the underlying disorder being treated such as cancer; it also includes the eradication and/or amelioration of one or more of the symptoms associated with the underlying disorder such that an improvement is observed in the subject, notwithstanding that the subject may still be afflicted with the underlying disorder. In some embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life).

As used herein, "administering" or "administration" of the compound of formula 6 or a pharmaceutically acceptable salt thereof encompasses the delivery to a patient a compound or a pharmaceutically acceptable salt thereof, or a prodrug or other pharmaceutically acceptable derivative thereof, using any suitable formulation or route of administration, e.g., as described herein.

As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount will vary depending on the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound.

As used herein, "patient" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys).

As used herein, "pharmaceutically acceptable" or "physiologically acceptable" refer to compounds, salts, compositions, dosage forms and other materials which are useful in preparing a pharmaceutical composition that is suitable for veterinary or human pharmaceutical use.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of Compound 6 include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus it may be pharmaceutically undesirable anions, such as iodide, oxalate, trifluoromethanesulfonate and the like, when such salts are chemical intermediates.

In some embodiments, provided herein is a pharmaceutical composition comprising GZD824 and optionally a pharmaceutically acceptable excipient.

In some embodiment, provided herein is a method for treating cancer in a patient in need thereof, comprising administering to the patient a therapeutically effective amount of a pharmaceutical composition comprising GZD824 and optionally a pharmaceutically acceptable excipient.

In some embodiments, provided herein is a medical use of a pharmaceutical composition comprising GZD824 and optionally a pharmaceutically acceptable excipient for manufacture of medicament for treating cancer.

In some embodiments, the cancer is hematological malignancy. In certain embodiments, the hematological malignancy is leukemia. In certain embodiments, the hematological malignancy is chronic myelogenous leukemia.

In certain embodiments, the patient has chronic myeloid leukemia that is resistant to current tyrosine kinase inhibitor therapies. In certain embodiments, the patient with chronic myeloid leukemia resistant to the current tyrosine kinase inhibitor therapies is caused by BCR-ABL mutations. In certain embodiments, BCR-ABL mutation is T315I, E255K/V, G250E, H396P, M351T, Q252H, Y253F/H, or BCR-ABL$^{WT}$ mutations. In certain embodiments, BCR-ABL mutation is T315I mutation.

In some embodiment, disclosed herein is GZD824 with high purity prepared by the method as shown in Scheme I.

In certain embodiments, the pharmaceutically composition comprising the GZD824 is administered once every one, two, or three days during the treatment cycle. The said treatment cycle may be 20-40 days, preferably 25-35 days, more preferably 28-day treatment cycle.

In certain embodiments, the pharmaceutical composition is administered once every other day, wherein the pharmaceutical composition comprising GZD824 in an amount of about 30 mg, about 40 mg, or about 45 mg.

In certain embodiments, pharmaceutical composition is administered once every other day, wherein the pharmaceutical composition comprising GZD824 in an amount of about 50 mg or about 60 mg.

In certain embodiments, pharmaceutical composition is formulated into a dosage unit to be administered every day, or once every other day (QOD), or once every three days, particularly once every other day.

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), VEEGUM®, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); and microcrystalline celluloses, such as AVICEL® PH-101, AVICEL® PH-103, AVICEL® PH-105, and AVICEL® RC-581. Suitable fillers include, but are not limited to, talc, calcium carbonate, microcrystalline cellulose, powdered cellulose, dextrates, kaolin, mannitol, silicic acid, sorbitol, starch, and pre-gelatinized starch. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; and algins. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; and silica or silica gels, such as AEROSIL® 200 and CAB-O-SIL®. The amount of a lubricant in the pharmaceutical composition provided herein varies upon the type of formulation, and is readily discernible to those of ordinary skill in the art. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes. A color lake is a combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, VEEGUM®, acacia, sodium carbomethylcellulose, hydroxypropyl methylcellulose, and polyvinylpyrrolidone. Suitable preservatives include, but are not limited to, glycerin, methyl and propylparaben, benzoic add, and sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from an active ingredient(s) in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient(s).

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient(s), and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These dosage forms can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical composition provided herein for oral administration can be formulated as immediate or modified release dosage forms, including delayed-, sustained, pulsed-, controlled, targeted-, and programmed-release forms.

In some embodiments, the present invention discloses a method for preparing GZD824 (a.k.a Compound 6) via conducting an amidation reaction with a compound of formula 4 and a compound of formula 5 in a solvent and in the presence of a base as shown below:

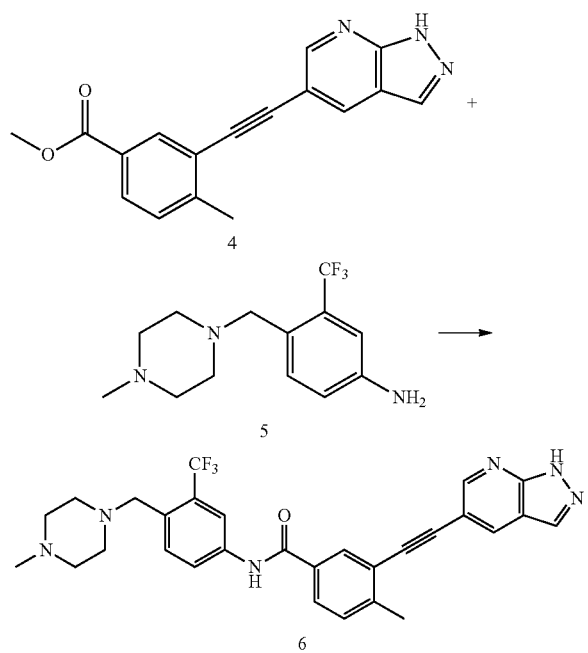

In some embodiments, the amidation reaction can be carried out under the protection of nitrogen or inert gas.

In some embodiments, the solvent in the amidation reaction is but not limited to an ether, DMF (N,N-dimethylformamide), N,N-dimethylacetamide, DMSO (dimethyl sulfoxide), N-methylpyrrolidone, toluene and acetonitrile, or a mixture thereof.

In some embodiments, the solvent in the amidation reaction is an ether, DMF, N,N-dimethylacetamide, N-methylpyrrolidone or toluene. In some embodiments, the solvent is an ether solvent.

In some embodiments, the ether solvent in the amidation reaction can be THF (tetrahydrofuran), 2-methyltetrahydrofuran or dioxane. In some embodiments, the ether solvent is THF.

In some embodiments, the amount of solvent in the amidation reaction can be a conventional amount used in the amidation reaction in the art, or the amount of solvent is in a volume/mass ratio of the solvent to the compound of formula 4, for example, (about 5 to about 17) mL:1 g, or for example, (about 10 to about 15) mL:1 g, or (about 15) mL:1 g.

In some embodiments, the base in the amidation reaction can be an organic base and/or an inorganic base.

In some embodiments, the organic base is but not limited to pyridine, an alkali metal salt of a $C_1$-$C_4$ alcohol and/or an amine such as —$N(R^1)(R^2)(R^3)$, wherein each of $R_1$, $R_2$ and $R_3$ independently represents hydrogen or a $C_1$-$C_4$ alkyl.

In some embodiments, the alkali metal salt of the $C_1$-$C_4$ alcohol is but not limited to a conventional alkali metal salt of a $C_1$-$C_4$ alcohol used in the amidation reaction in the art, such as potassium tert-butoxide and/or sodium tert-butoxide.

In some embodiments, —$N(R^1)(R^2)(R^3)$ is $Et_3N$, DIPEA, (i-Pr)$_2$NH and Bu$_3$N, such as $Et_3N$ or (i-Pr)$_2$NH, typically, $Et_3N$.

In some embodiments, the inorganic base is but not limited to an alkali metal carbonate and/or an alkali metal hydroxide.

In some embodiments, the alkali metal carbonate is, for example, $K_2CO_3$ and/or $Cs_2CO_3$.

In some embodiments, the alkali metal hydroxide is, for example, NaOH and/or KOH.

In some embodiments, the amount of the base used in the amidation reaction can be a conventional amount used in the amidation reaction in the art. In some embodiments, The molar ratio of a base to the compound of formula 4 is, for example, (about 1.5 to about 10):1, for example, (about 1.5 to about 8.0):1, for example, (about 1.5 to about 6):1, for example, (about 1.5 to about 5.0):1.

In some embodiments, in the amidation reaction, the base can be added to the mixture composed of the rest of the materials in batches.

In some embodiments, the molar ratio of the compound of formula 5 to the compound of formula 4 is, for example, (about 0.8 to about 1.5):1, for example, (about 0.9 to about 1.3):1, for example (about 1.2 to about 1.3):1.

In some embodiments, the reaction temperature of the amidation reaction is, for example, within a range about from about −80° C. to about 10° C., such as about −65° C. to about −60° C., about −60° C. to about −40° C., about −30° C. to about −20° C., about −20° C. to −about 15° C., or about 0° C. to about 10° C.

In some embodiments, the process of the amidation reaction can be monitored by TLC, HPLC, and other methods known to a person skilled in the art. A person skilled in the art can assess the completion of the reaction according to the reaction scale, the conversion rate of raw materials, the efficiency of the reaction (i.e. the relationship between the yield and the reaction time), the formation of impurities and so on to obtain the preferred yield and purity. The reaction time is within a range from about 2 h to about 20 h, for example, about 2 h to about 12 h. In some embodiments, the reaction time is about 2 h to about 4 h.

In some embodiments, the post-treatment of the amidation reaction can be a conventional post-treatment used in the amidation reaction in the art, which can comprise washing the reaction solution with water and saturated brine sequentially, removing the solvent, slurrying with water, filtering and drying.

In some embodiments, after post-treatment of the reaction mixture with saturated brine while before the removal of the solvent, the reaction mixture can immediately be mixed with an amino acid compound, followed by washed with saturated brine.

In some embodiments, the amino acid compound is cysteine, N-acetyl-L-cysteine, ethylenediaminetetraacetic acid, sodium edetate and dithiocarbamates, such as cysteine or N-acetyl-L-cysteine, typically, N-acetyl-L-cysteine.

In some embodiments, the molar ratio of the amino acid compound to the compound of formula 4 is about 0.7 to 1.0:1.

In some embodiments, the method for removing the solvent can be concentrated under reduced pressure.

In some embodiments, the amidation reaction is carried out under the protection of nitrogen or inert gas, the solvent comprises DMF and/or THF, the base comprises potassium tert-butoxide, sodium tert-butoxide, or $Et_3N$, the molar ratio of the base to the compound of formula 4 is (about 1.5 to 6):1, the molar ratio of the compound of formula 5 to the compound of formula 4 is (about 0.8 to 1.5):1, and the amidation reaction is conducted at from about −60° C. to about 10° C.

In some embodiments, the compound of formula 4 is prepared by deprotection of a compound of formula 3 in a solvent as shown below;

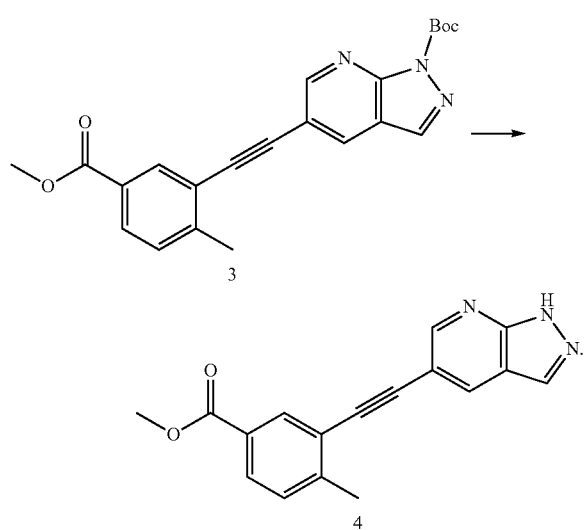

In some embodiments, the deprotection reaction can be carried out under the protection of nitrogen or inert gas.

In some embodiments, the deprotection reaction can be carried out in the presence of an acid. In some embodiments, the acid can be, but not limited to, hydrochloric acid, trifluoroacetic acid and p-toluenesulfonic acid.

When the deprotection reaction is carried out in the presence of the acid, the solvent can be a conventional solvent used in the deprotection reaction under this condition, and it can be a $C_1$-$C_4$ alcohol (e.g. methanol and/or ethanol, typically, methanol), chloroalkane(s), THF, or acetonitrile.

In some embodiments, the deprotection reaction can be carried out in the absence of an acid. For example, the raw materials of the deprotection reaction only consist of the solvent and the compound of formula 3.

When the deprotection reaction is carried out in the absence of the acid (for example that the raw materials of the deprotection reaction only consist of the solvent and the compound of formula 3), the solvent can be a solvent conventionally used in the deprotection reaction under this condition. It can be, but not limited to, acetonitrile, a mixture solvent of acetonitrile and water, or a mixture solvent of a $C_1$-$C_4$ alcohol and water, wherein, the mass ratio of the $C_1$-$C_4$ alcohol to water is about, for example, 3 to 5:1; the $C_1$-$C_4$ alcohol comprises, for example, methanol, ethanol, isopropanol, or mixture thereof such as methanol and/or ethanol. In some embodiments, the solvent is methanol. In some embodiments, the mixed solvent of a $C_1$-$C_4$ alcohol and water is, for example, a mixed solvent of methanol and water with a mass ratio of 3:1, typically a mixed solvent of a $C_1$-$C_4$ alcohol and water.

In some embodiments, in the deprotection reaction, the mass ratio of the solvent to the compound of formula 3 is, for example, (about 10 to about 15):1.

In some embodiments, the reaction temperature of the deprotection reaction is, for example, within a range from about 30° C. to about 80° C., such as about 60° C. to about 80° C., about 60° C. to about 70° C., or about 60° C. to about 65° C.

In some embodiments, the process of the deprotection reaction can be monitored by TLC, HPLC and other methods known to a person skilled in the art. A person skilled in the art can assess the completion of the reaction according to the reaction scale, the conversion rate of raw materials, the efficiency of the reaction (i.e. the relationship between the yield and the reaction time), the formation of impurities and so on to obtain the preferred yield and purity. The reaction time is, for example, within a range from about 10 h to about 36 h, such as about 10 h to about 18 h.

In some embodiments, the post-treatment of the deprotection reaction can comprise cooling and filtering.

In some embodiments, the temperature to be achieved by cooling can be about 20° C. to about 25° C.

In some embodiments, the post-treatment can further comprise drying and recrystallizing immediately and subsequently after filtering, and it can also directly be subjected to recrystallizing without drying. The method for recrystallizing can be dissolving by heating and precipitating by cooling.

In some embodiments, the solvent used in the recrystallizing is, but not limited to for example, a $C_1$-$C_4$ alcohol, for further example, the solvent comprises methanol, ethanol, isopropanol, or mixture thereof. In some embodiments, the solvent is methanol or ethanol. In some embodiments, the solvent is methanol.

In some embodiments, the mass ratio of the solvent used in the recrystallizing to the compound of formula 4 can be (about 5 to about 15):1, such as (about 5 to about 10):1.

In some embodiments, in the method of dissolving by heating and precipitating by cooling, the temperature for dissolving is, for example within a range from about 50° C. to about 70° C., such as about 60° C. to about 70° C.

In some embodiments, in the method of dissolving by heating and precipitating by cooling, the cooling can be slow cooling, rapid cooling or gradient cooling. In some embodiments, it can be gradient cooling. The temperature can be reduced by about 5° C. per 1 h to 1.5 h. The gradient cooling can be started at a temperature of about 40° C. to about 50° C.

A person skilled in the art can evaluate the completion of the reaction according to the precipitation conditions and so on to obtain a preferred yield and purity. The recrystallizing time is, for example within a range from about 8 h to about 40 h, such as about 8 h to about 10 h.

In some embodiments, the deprotection reaction can be carried out under the protection of nitrogen or inert gas, the raw materials of the deprotection reaction can only consist of the solvent and the compound of formula 3, the solvent is a mixture of a $C_1$-$C_4$ alcohol and water, the temperature of the deprotection reaction is within a range from about 60° C. to about 65° C.

In some embodiments, the compound of formula 3 can be prepared via a Sonogashira coupling reaction with a compound of formula 1 and a compound of formula 2 in a solvent and in the presence of a base, a catalyst and a catalyst ligand as shown below:

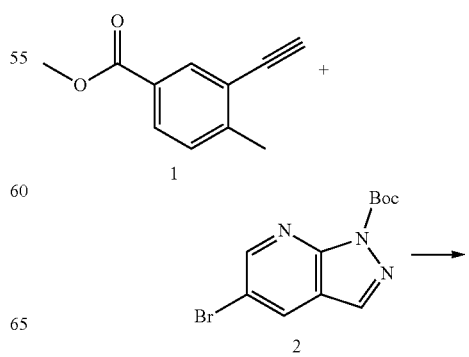

-continued

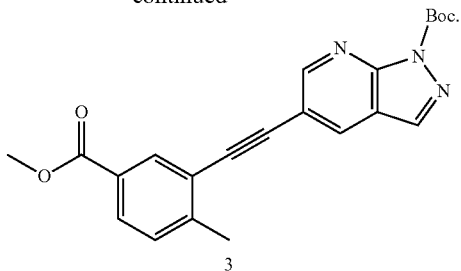

3

In some embodiments, the Sonogashira reaction can be carried out under the protection of nitrogen or inert gas.

In some embodiments, the solvent in the Sonogashira reaction, can be a conventional solvent used in the Sonogashira reaction in the art, for example that (1) comprises N-methylpyrrolidone, DMSO (dimethyl sulfoxide), DMF (N,N-dimethylformamide), N,N-dimethylacetamide, acetonitrile, toluene, dioxane and THF (tetrahydrofuran), (2) N-methylpyrrolidone, DMSO (dimethyl sulfoxide), DMF (N,N-dimethylformamide), N,N-dimethyl acetamide or acetonitrile; or (3) N-methylpyrrolidone, DMF (N,N-dimethylformamide) or N,N-dimethylacetamide.

In some embodiments, the volume/mass ratio of the solvent to the compound of formula 2 is, for example, (about 5 to about 10) mL:1 g, such as (about 7 to about 10) mL:1 g.

In some embodiments, in the Sonogashira reaction, the catalyst can be a conventional catalyst used in the Sonogashira reaction in the art, such as a palladium catalyst. The palladium catalyst can comprise $PdCl_2(PPh_3)_2$, $Pd(dppf)_2Cl_2$, $Pd(dppf)_2Cl_2$ and/or palladium carbon. In some embodiments, the catalyst is $PdCl_2(PPh_3)_2$ or $Pd(dppf)_2Cl_2$.

In some embodiments, the molar ratio of the catalyst to the compound of formula 2 is, for example, (about 0.01 to about 0.05):1, such as (about 0.01 to about 0.03):1.

In some embodiments, a catalyst ligand used in the Sonogashira reaction comprises, for example, a copper compound and/or triphenylphosphine. In some embodiments, the copper compound can be, for example, CuI, CuBr, $Cu_2O$, CuO and/or Cupric acetate. In some embodiments, the catalyst ligand is CuI or CuBr.

In some embodiments, the molar ratio of the catalyst ligand to the catalyst is, for example, (about 0.8 to about 1.2):1. In some embodiments, the molar ratio of the catalyst ligand to the catalyst is 1:1.

In some embodiments, in the Sonogashira reaction, the base can be, for example an organic base and/or an inorganic base.

In some embodiments, the organic base can be a conventional organic base used in the Sonogashira reaction in the art, for example that it comprises pyridine, an alkali metal salt of a $C_1$-$C_4$ alcohol, and/or
—N($R^4$)($R^5$)($R^6$), wherein each of $R^4$, $R^5$ and $R^6$ independently represents hydrogen or a $C_1$-$C_4$ alkyl.

In some embodiments, the alkali metal salt of the $C_1$-$C_4$ alcohol can be, but not limited to potassium tert-butoxide and/or sodium tert-butoxide.

In some embodiments, the —N($R^4$)($R^5$)($R^6$), for example, comprises $Et_3N$, DIPEA, (i-Pr)$_2$NH and/or $Bu_3N$. In some embodiments, the —N($R^4$)($R^5$)($R^6$) is $Et_3N$ or DIPEA. In some embodiments, the —N($R^4$)($R^5$)($R^6$) is $Et_3N$.

In some embodiments, the inorganic base can be a conventional inorganic base used in the Sonogashira reaction in the art, for example, it comprises an alkali metal carbonate and/or an alkali metal hydroxide.

In some embodiments, the alkali metal carbonate is, for example, $K_2CO_3$ and/or $Cs_2CO_3$.

In some embodiments, the alkali metal hydroxide is, for example, NaOH and/or KOH.

In some embodiments, in the Sonogashira reaction, the molar ratio of the base to the compound of formula 2 is, for example, (about 1.0 to about 1.5):1. In some embodiments, the molar ration is, (about 1.2 to about 1.3):1.

In some embodiments, in the amidation reaction, the molar ratio of the compound of formula 1 to the compound of formula 2 is, for example, (about 0.95 to about 2.0):1, such as (about 1.2 to about 1.5):1. In some embodiments, the molar ration is (about 1.2 to about 1.3):1.

In some embodiments, the reaction temperature of the Sonogashira reaction is, for example, about 40° C. to about 80° C., such as about 65° C. to about 75° C., typically, about 65° C. to about 70° C.

The process of the Sonogashira reaction can be monitored by TLC, HPLC and other methods known to a person skilled in the art. A person skilled in the art can evaluate the completion of the reaction according to the reaction scale, the conversion rate of raw materials, the efficiency of the reaction (i.e. the relationship between the yield and the reaction time), the formation of impurities and so on to obtain the preferred yield and purity. The reaction time is, for example, within a range from about 2 h to about 12 h, such as about 2 h to about 5 h. In some embodiments, it is about 2 h to about 3 h.

In some embodiments, the post-treatment of the Sonogashira reaction can be a conventional post-treatment used in the amidation reaction in the art, which comprise mixing with water and filtering.

In some embodiments, the post-treatment of the Sonogashira reaction can further comprise mixing with an amino acid compound before mixing with water.

In some embodiments, the amino acid compound used for removing heavy metals comprises but not limited to, for example, cysteine, N-acetyl-L-cysteine, ethylenediaminetetraacetic acid, sodium edetate and/or dithiocarbamates. In some embodiments, the amino acid compound is cysteine or N-acetyl-L-cysteine. In some embodiments, the amino acid compound is N-acetyl-L-cysteine.

In some embodiments, the molar ratio of the amino acid compound to the compound of formula 2 is, for example, (about 0.1 to about 0.5):1.

In some embodiments, the temperature subjected to mixing with an amino acid compound can be within a range from about 35° C. to about 45° C.

In some embodiments, the mixing time subjected to mixing with an amino acid compound can be about 4 h to about 5 h.

In some embodiments, the mixing temperature subjected to mixing with water can be within a range from about 20° C. to about 25° C.

In some embodiments, the process of filtering can further comprise washing with water.

In some embodiments, the post-treatment of the Sonogashira reaction can further comprise slurrying right after filtering.

In some embodiments, the solvent used for slurrying can be, but not limited to, ethyl acetate and n-heptane. The volume ratio of the ethyl acetate to the n-heptane can be about 1:1.

In some embodiments, the volume/mass ratio of the solvent to the crude filter cake used in the slurrying can be (about 5 to about 7) mL:1 g.

In some embodiments, the Sonogashira reaction can be carried out under the protection of nitrogen or inert gas, the solvent is N-methylpyrrolidone, DMF or acetonitrile, the catalyst is PdCl$_2$(PPh$_3$)$_2$ or Pd(dppf)$_2$Cl$_2$, the molar ratio of the catalyst to the compound of formula 2 is (about 0.01 to about 0.05):1, the catalyst ligand is CuI or CuBr, the molar ratio of the catalyst ligand to the catalyst is (about 0.8 to about 1.2):1, the base is Et$_3$N, the molar ratio of the base to the compound of formula 2 is, for example, (about 1.0 to about 1.5):1, the molar ratio of the compound of formula 1 to the compound of formula 2 is, for example, (about 0.95 to about 1.3):1, the temperature of the Sonogashira reaction is about 65° C. to about 75° C.

In some embodiments, a compound of formula 4 can be prepared via a deprotection reaction of the compound of formula 3 in a solvent as shown below:

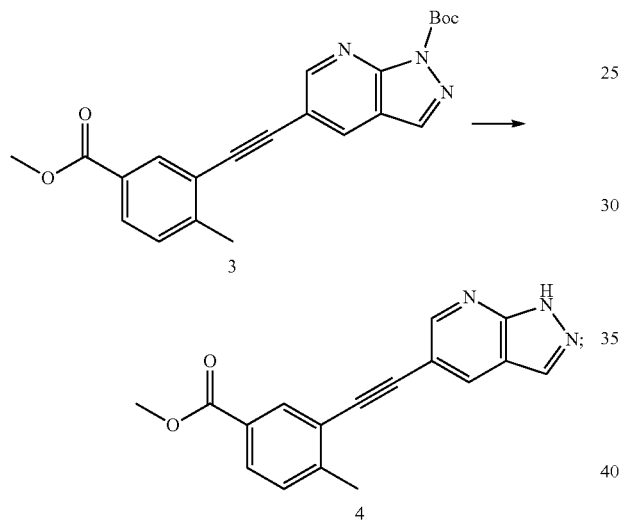

the reaction conditions of the deprotection reaction can refer to those as described above.

In some embodiments, the compound of formula 3 can be prepared via a Sonogashira coupling reaction with a compound of formula 1 and a compound of formula 2 in a solvent and in the presence of a base, a catalyst and a catalyst ligand as shown below:

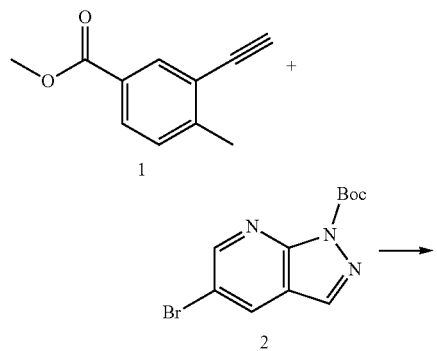

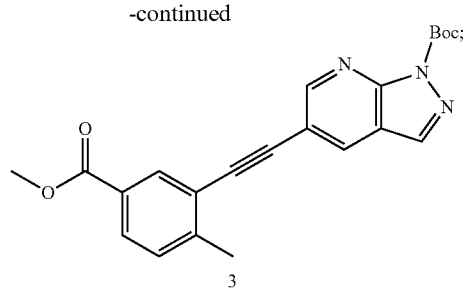

the conditions of the Sonogashira reaction can refer to those as described above.

In some embodiments, the present invention also provides a compound of formula 3 or a compound of formula 4,

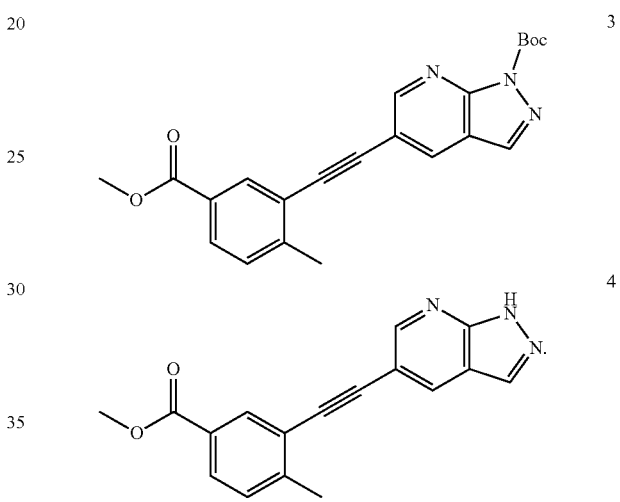

Without violating the common knowledge in the art, embodiments in the present invention may be combined.

The reagents and raw materials employed in the present invention are commercially available.

In some embodiments, the present invention provides a compound of formula 6 prepared by the methods described herein.

The advantageous effects achieved by the present invention are as follows:
  i. The present invention adopts a new design route. According to the structural characteristics of the compound GZD824, the present invention selects inexpensive and readily available reaction raw materials, utilizes convenient operation and mild reaction conditions, avoids the use of harsh reaction equipment such as sealed tube, simplify the post-treatment with the only requirement of recrystallization and prevent multiple column chromatography, and can meet the requirements of industrial production.
  ii. The present invention has novel design route and shorter reaction route. It only requires three steps of the reaction to obtain the target product. Compared with the existing route, the present invention has shortened reaction route, reduced expensive and complex raw materials, and achieves advantages such as high yield, good purity and controllable cost, etc. The present invention utilizes multiple in-process control in the reaction process, which can effectively ensure the quality of the intermediates and the subsequent final product.

iii. During the early stage of the present invention, amino acids are added for several times in process of the coupling and amidation reaction in order to prevent the excess of the heavy metal, which is environment friendly and effectively ensures that the heavy metal contained in the active pharmaceutical ingredient meets the standard of the pharmacopoeia.

iv. The present invention adopts a new design route to obtain two new intermediates which are the compound of formula 3 and the compound of formula 4.

Examples

The following examples further illustrate, but not limit to, the present invention. It should be noted that, a person skilled in the art, without departing from the inventive concept of the present invention, may make several modifications and improvements, which all include to the protection scope of the present invention.

The specific conditions that haven't been disclosed in the experimental methods of the following examples may be selected according to conventional methods and conditions, or according to product specifications.

Unless otherwise specified, "room temperature" in the following examples refers to 20° C. to 25° C. The term "h" used herein refers to hour or hours.

Embodiment 1

Step 1:

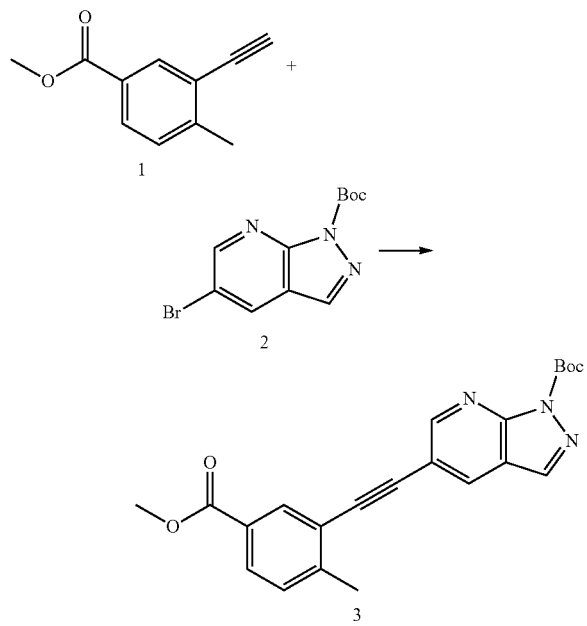

Under the protection of nitrogen, N-methylpyrrolidone (137.6 g) was heated to 30 to 35° C., and a compound of formula 1 (14.4 g, 1.3 eq), a compound of formula 2 (19.14 g, 1 eq), bis(triphenylphosphate)palladium dichloride (0.46 g, 0.01 eq) and cuprous iodide (0.113 g, 0.01 eq) were added sequentially thereto, and then triethylamine (9.45 g, 1.5 eq) was added thereto under the protection of nitrogen. The reaction mixture was heated to 65 to 75° C. and kept at this temperature for 2 hours. In-process control of the reaction was performed by liquid phase detection. When the content of the compound of formula 2 was <0.1%, the reaction was terminated. After the reaction was terminated, the reaction solution was cooled to 35 to 45° C., and N-acetyl-L-cysteine (1 g, 0.1 eq) was added thereto directly. The reaction was performed under stirring for 4 to 5 h. The resultant product was cooled to room temperature, precipitated by adding water, centrifuged, and washed with purified water to obtain a crude filter cake. After the crude filter cake was dried under vacuum, a mixture of ethyl acetate and n-heptane (wherein the volume ratio of ethyl acetate to n-heptane was 1:1, and 5 mL of the mixed solvent of ethyl acetate and n-heptane was used per gram of the crude filter cake) was added to the crude filter cake and slurried. The obtained slurry was dried under vacuum to give a compound of formula 3 with a yield of 85.97% and a purity of 98.2%.

The NMR data of the compound of formula 3 is $^1$HNMR (400 MHz, d-DMSO): δ ppm: 8.93 (1H, d, J=2.0 Hz); 8.63 (1H, d, J=2.0 Hz); 8.49 (1H, s); 8.11 (1H, d, J=2.0 Hz); 7.92 (1H, dd, J1=1.6 Hz; J2=8.0 Hz); 7.52 (1H, d, J=8.0 Hz); 3.88 (3H, s); 2.59 (3H, s); 1.65 (9H, s).

Step 2:

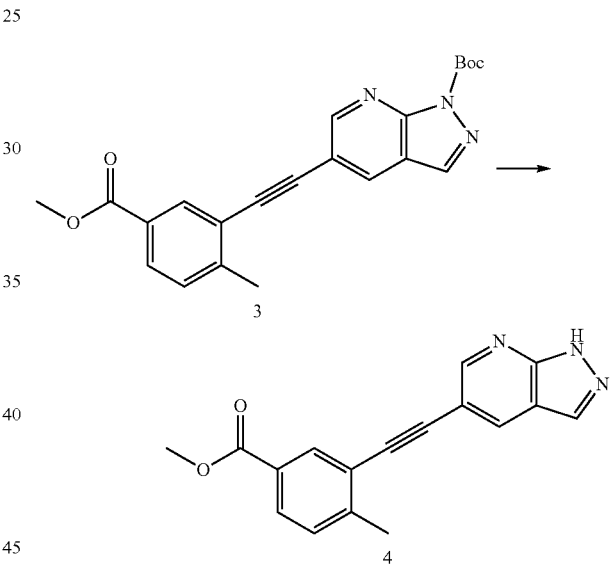

Under the protection of nitrogen, methanol (160 g) and water (50 g) were added to a compound of formula 3 (20 g, 1.0 eq) sequentially, the reaction system was stirred under reflux for 18 hours and in-process control thereof was performed. The resultant product was cooled to room temperature, and filtered to obtain a filter cake (without oven-drying). Methanol with a mass of 10 times that of the filter cake was added thereto for recrystallization, the obtained mixture was stirred at 60 to 70° C. for 8 to 10 h, then cooled to 40 to 50° C., and subjected to a gradient cooling process with a cooling rate of 5° C. per 1 to 1.5 h to generate a solid precipitate slowly. The obtained mixture was filtered and the filter cake was washed with methanol and dried under vacuum to obtain a compound of formula 4, with a yield of 91% and a purity of 99.7%.

The NMR data of the compound of formula 4 is $^1$HNMR (400 MHz, d-DMSO): δ ppm: 8.73 (1H, d, J=2.0 Hz); 8.52 (1H, t, J=2.0 Hz); 8.21 (1H, d, J=2.0 Hz); 8.06 (1H, s); 7.86 (1H, dd, J1=2.0 Hz; J2=8.0 Hz); 7.49 (1H, dd, J1=1.6 Hz; J2=7.6 Hz); 3.86 (3H, s); 2.56 (3H, s).

Step 3:

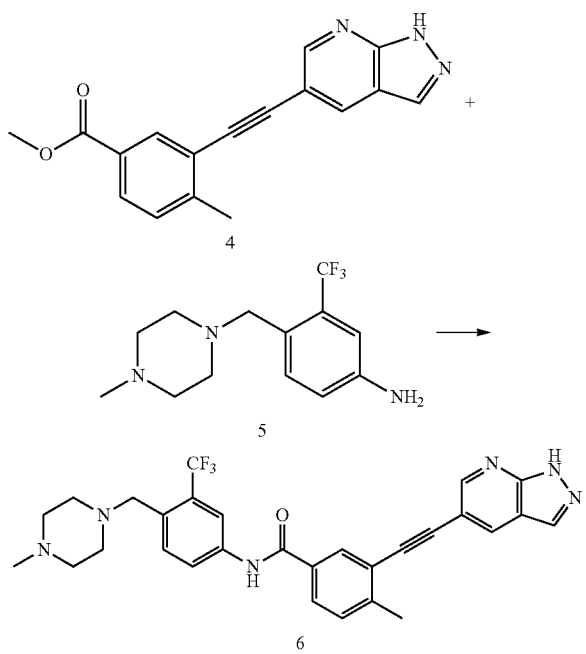

Under the protection of nitrogen, THF (448 mL), a compound of formula 4 (29.1 g, 1 eq) and a compound of formula 5 (24.6 g, 0.9 eq) were added, and the mixture was cooled under stirring to −65° C. to −60° C. At this temperature, potassium tert-butoxide (19 g×3) was added at intervals of 0.5 h in batches. In-process control of the reaction was performed by liquid phase detection. After 2 hours, the temperature of the reaction was raised to −5 to 0° C. The reaction solution was washed with purified water, stirred for 0.5 to 1 hour, washed with brine, and partitioned to obtain an organic phase. The organic phase was added with N-acetyl-L-cysteine (11.41 g, 0.7 eq), stirred, washed with brine to neutralization, and concentrated under reduced pressure. The resultant filter cake was washed with purified water, and slurried. The resultant product was washed with purified water again and dried under vacuum to obtain a compound of formula 6, with a yield of 88.2% and a purity of 98.6%.

The NMR data of the compound of formula 6 is $^1$H NMR (400 MHz, d-DMSO): δ ppm: 10.53 (1H, s); 8.75 (d, J=2.0); 8.53 (d, J=2.4); 8.24 (1H, s); 8.23 (d, J=2.4); 8.21 (d, J=1.6); 8.09 (dd, J1=1.6; J2=8.4); 7.94 (dd, J1=2.0; J2=8.0); 7.71 (d, J=8.8); 7.53 (d, J=8.0); 3.56 (2H, s); 2.59 (3H, s); 2.34-2.35 (8H, m), 2.16 (3H, s);

The carbon spectrum data thereof is $^{13}$C NMR (100 MHz, d-DMSO): δ ppm: 20.38, 45.65, 52.64, 54.67, 57.41, 88.26, 91.86, 111.76, 113.98, 117.19, 122.14, 123.43, 127.35 (q), 124.30 (q), 128.10, 129.89, 130.49, 131.15, 132.02, 132.13, 132.93, 133.66, 138.15, 143.65, 150.55, 164.64.

Embodiment 2

The Sonogashira reaction was carried out with reference to the reaction parameters in each row of Table 1 (the other parameters are the same as those in the first step of embodiment 1), the yield calculated according to the compound of formula 2 is shown in the last column of Table 1.

TABLE 1

| Molar ratio of the compound of formula 1 to the compound of formula 2 | Palladium catalyst and amount/eq | Ligand and amount/eq | Solvent | Type and amount of the base | Reaction temperature. reaction time | Yield |
| --- | --- | --- | --- | --- | --- | --- |
| 1.2:1 | PdCl$_2$(PPh$_3$)$_2$ 0.01 | CuI 0.01 | DMF | Et$_3$N 1.5eq | 65 to 75° C. 5 h | 83.63% |
| 1.2:1 | Pd (dppf)$_2$Cl$_2$ 0.01 | CuI 0.01 | N-methylpyrrolidone | Et$_3$N 1.5eq | 65 to 70° C. 5 h | 79.32% |
| 1.2:1 | PdCl$_2$(PPh$_3$)$_2$ 0.01 | CuI 0.01 | N-methylpyrrolidone | Et$_3$N 1.5eq | 65 to 70° C. 3 h | 83.04% |
| 1.2:1 | PdCl$_2$(PPh$_3$)$_2$ 0.01 | CuI 0.01 | N-methylpyrrolidone | Et$_3$N 1.5eq | 65 to 75° C. 2 h | 85.44% |
| 1.2:1 | PdCl$_2$(PPh$_3$)$_2$ 0.01 | CuI 0.01 | DMF | DIPEA 1.5eq | 65 to 75° C. 5 h | 77.91% |
| 1.2:1 | Pd(dppf)$_2$Cl$_2$ 0.01 | CuI 0.01 | Acetonitrile | Et$_3$N 1.5eq | 65 to 75° C. 5 h | 80.77% |
| 1.2:1 | Pd(dppf)$_2$Cl$_2$ 0.01 | CuI 0.01 | Toluene | Et$_3$N 1.5eq | 65 to 75° C. 2 h | 74.22% |
| 1.2:1 | Pd(dppf)$_2$Cl$_2$ 0.01 | CuI 0.01 | Dioxane | Et$_3$N 1.5eq | 65 to 75° C. 2 h | 77.59% |

Embodiment 3

The amidation reaction was carried out with reference to the reaction parameters in each row of Table 2 (the other parameters are the same as those in the third step of embodiment 1), the yield calculated on the basis of the compound of formula 4 or 5 which is with a smaller molar amount is shown in the last column of Table 2.

TABLE 2

| Molar ratio of the compound of formula 4 to the compound of formula 5 | Reaction temperature | Solvent | Type and amount of the base | Reaction time | Yield |
|---|---|---|---|---|---|
| 1:1.3 | −15 to −20° C. | THF | t-BuOK 6eq | 20 h | 92.89% |
| 1:1.2 | −15 to −20° C. | THF | t-BuOK 5eq | 12 h | 93.65% |
| 1:1.2 | 0 to 10° C. | THF | t-BuOK 5eq | 2 h | 92.48% |
| 1:1.2 | −60 to −40° C. | THF | Et$_3$N 1.5eq | 12 h | 84.81% |
| 1.3:1 | −60 to −40° C. | THF | Et$_3$N 1.5eq | 2 h | 95.56% |
| 1:1.2 | −60 to −40° C. | DMF | t-BuOK 5eq | 2 h | 94.33% |
| 1.3:1 | −30° C. to −20° C. | Toluene | (i-Pr)$_2$NH | 12 h | 89.72% |

What is claimed is:

1. A process for preparing a compound of formula 6:

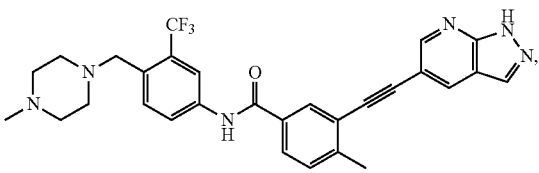

6 comprising step 3: reacting a compound of formula 4:

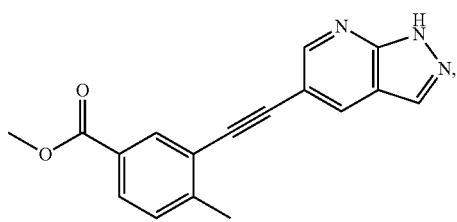

4 with a compound of formula 5:

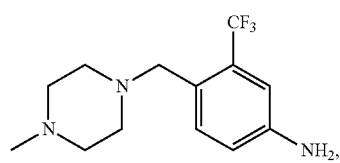

5 in a solvent and in the presence of a base.

2. The process of claim 1, wherein step 3 is carried out under the protection of nitrogen or inert gas;

and/or, in step 3, the solvent comprises ether solvents, N,N-dimethylformamide (DMF), N,N-dimethylacetamide, dimethyl sulfoxide (DMSO), N-methylpyrrolidone, toluene or acetonitrile;

and/or, in step 3, the volume/mass ratio of the solvent to the compound of formula 4 is (5 to 17) mL: 1 g;

and/or, in step 3, the base is an organic base and/or an inorganic base;

and/or, in step 3, the molar ratio of the base to the compound of formula 4 is (1.5 to 10):1;

and/or, in step 3, the base is added to the mixture composed of the rest materials in batches;

and/or, in step 3, the molar ratio of the compound of formula 5 to the compound of formula 4 is (0.8 to 1.5):1;

and/or, the reaction temperature of step 3 is from −80° C. to 10° C.;

and/or, the post-treatment of step 3 comprises washing the reaction solution with water and saturated brine sequentially, removing the solvent, slurrying with water, filtering and drying.

3. The process of claim 2, wherein in step 3, the solvent is ether solvents, DMF, N,N-dimethylacetamide, N-methylpyrrolidone or toluene;

and/or, in step 3, when the solvent includes an ether solvent, the ether solvent comprises tetrahydrofuran (THF), 2-methyltetrahydrofuran or dioxane;

and/or, in step 3, the volume/mass ratio of the solvent to the compound of formula 4 is (10 to 15) mL:1 g;

and/or, in step 3, when the base includes an organic base, the organic base comprises pyridine, an alkali metal salt of a $C_1$-$C_4$ alcohol, or —N($R^1$)($R^2$)($R^3$), wherein each of $R_1$, $R_2$, and $R_3$ independently represents hydrogen or a $C_1$-$C_4$ alkyl;

and/or, in step 3, when the base includes an inorganic base, the inorganic base comprises an alkali metal carbonate and/or an alkali metal hydroxide;

and/or, in step 3, the molar ratio of the base to the compound of formula 4 is (1.5 to 8.0):1;

and/or, in step 3, when the base is added to the mixture composed of the rest materials in batches, the number of the batch are three;

and/or, in step 3, the molar ratio of the compound of formula 5 to the compound of formula 4 is (0.9 to 1.3):1;

and/or, the reaction temperature of step 3 is from −65° C. to −60° C., −60° C. to −40° C., −30° C. to −20° C., −20° C. to −15° C. or 0° C. to 10° C.;

and/or, when the post-treatment of step 3 comprises washing the reaction solution with water and saturated brine sequentially, removing the solvent, slurrying with water, filtering and drying, it further comprises mixing the reaction solution with an amino acid compound, followed by washing with saturated brine sequentially and immediately after washing the reaction solution with saturated brine while before the removal of the solvent;

and/or, when the post-treatment of step 3 comprises washing the reaction solution with water and saturated brine sequentially, removing the solvent, slurrying with water, filtering and drying, the method for removing the solvent is concentrating under reduced pressure;

and/or, when the post-treatment of step 3 comprises washing the reaction solution with water and saturated brine sequentially, removing the solvent, slurrying with water, filtering and drying, it further comprises filtering, followed by washing with water sequentially and immediately after the removal of the solvent while before slurrying with water.

4. The process of claim 3, wherein in step 3, the solvent is an ether solvent;

and/or, in step 3, when the solvent includes an ether solvent, the ether solvent is THF;

and/or, in step 3, the volume/mass ratio of the solvent to the compound of formula 4 is 15 mL:1 g;

and/or, in step 3, when the base includes an organic base and the organic base includes an alkali metal salt of a $C_1$-$C_4$ alcohol, the alkali metal salt of the $C_1$-$C_4$ alcohol is potassium tert-butoxide and/or sodium tert-butoxide;

and/or, in step 3, when the base includes an organic base and the organic base includes —N($R^1$)($R^2$)($R^3$), the —N($R^1$)($R^2$)($R^3$) is $Et_3N$, N,N-Diisopropylethylamine (DIPEA), (i-Pr)$_2$NH or $Bu_3N$;

and/or, in step 3, when the base includes an inorganic base and the inorganic base includes an alkali metal carbonate, the alkali metal carbonate is $K_2CO_3$ and/or $Cs_2CO_3$;

and/or, in step 3, when the base includes an inorganic base and the inorganic base includes an alkali metal hydroxide, the alkali metal hydroxide is NaOH and/or KOH;

and/or, in step 3, the molar ratio of the base to the compound of formula 4 is (1.5 to 6.0):1;

and/or, in step 3, the molar ratio of the compound of formula 5 to the compound of formula 4 is (1.2 to 1.3):1;

and/or, when the post-treatment of step 3 comprise washing the reaction solution with water and saturated brine sequentially, removing the solvent, slurrying with water, filtering and drying and further comprises mixing the reaction solution with an amino acid compound, followed by washing with saturated brine sequentially and immediately after washing the reaction solution with saturated brine while before the removal of the solvent, the amino acid compound is selected from the group consisting of cysteine, N-acetyl-L-cysteine, ethylenediaminetetraacetic acid, sodium edetate and dithiocarbamates;

and/or, when the post-treatment of step 3 comprises washing the reaction solution with water and saturated brine sequentially, removing the solvent, slurrying with water, filtering and drying and further comprises mixing the reaction solution with an amino acid compound, followed by washing with saturated brine sequentially and immediately after washing the reaction solution with saturated brine while before the removal of the solvent, the molar ratio of the amino acid compound to the compound of formula 4 is (0.7 to 1.0):1.

5. The process of claim 4, wherein in step 3, when the base includes an organic base and the organic base includes —N($R^1$)($R^2$)($R^3$), the —N($R^1$)($R^2$)($R^3$) is $Et_3N$ or DIPEA;

and/or, in step 3, the molar ratio of the base to the compound of formula 4 is (1.5 to 5.0):1;

and/or, when the post-treatment of step 3 comprises washing the reaction solution with water and saturated brine sequentially, removing the solvent, slurrying with water, filtering and drying and further comprises mixing the reaction solution with an amino acid compound, followed by washing with saturated brine sequentially and immediately after washing the reaction solution with saturated brine while before the removal of the solvent, the amino acid compound is cysteine or N-acetyl-L-cysteine.

6. The process of claim 1, wherein the compound of formula 4 is prepared by a process comprising step 2: converting a compound of formula 3:

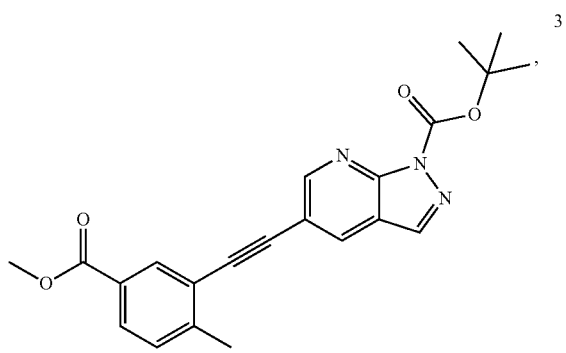 [SMILES: COC(=O)c1ccc(C)c(C#Cc2cnc3c(cnn3C(=O)OC(C)(C)C)c2)c1]

to the compound of formula 4 in a solvent, and wherein:
(i) step 2 is carried out in the absence of the acid, the solvent is acetonitrile, a mixed solvent of acetonitrile and water or a mixed solvent of a $C_1$-$C_4$ alcohol and water; or
(ii) step 2 is carried out in the presence of an acid.

7. The process of claim 6, wherein step 2 is carried out under the protection of nitrogen or inert gas;

and/or, step 2 is carried out in the absence of an acid;

and/or, in step 2, the mass ratio of the solvent to the compound of formula 3 is (10 to 15):1;

and/or, the temperature of step 2 is from 30° C. to 80° C.;

and/or, the post-treatment of step 2 comprises cooling and filtering.

8. The process of claim 7, wherein
when step 2 is carried out in the absence of the acid, the solvent is acetonitrile, a mixed solvent of acetonitrile and water or a mixed solvent of a $C_1$-$C_4$ alcohol and water;

and/or, the temperature of step 2 is from 60° C. to 80° C.;

and/or, when the post-treatment of step 2 comprises cooling to a temperature of 20° C. to 25° C., and filtering;

and/or, when the post-treatment of step 2 comprises cooling, and filtering, the post-treatment further comprises drying and recrystallizing sequentially and immediately after filtering, or recrystallizing without drying after filtering.

9. The process of claim 8, wherein when step 2 is carried out in the absence of the acid, the solvent is a mixed solvent of a $C_1$-$C_4$ alcohol and water;

and/or, when step 2 is carried out in the absence of the acid and the solvent is a mixed solvent of a $C_1$-$C_4$ alcohol and water, the mass ratio of the $C_1$-$C_4$ alcohol to the water is (3 to 5):1;

and/or, when step 2 is carried out in the absence of the acid and the solvent is a mixed solvent of a $C_1$-$C_4$ alcohol and water, the $C_1$-$C_4$ alcohol comprises methanol, ethanol or isopropanol;

and/or, the temperature of step 2 is 60° C. to 70° C.;

and/or, when the post-treatment of step 2 comprises cooling and filtering and further comprises drying and recrystallizing sequentially and immediately after filtering, or recrystallizing without drying directly after filtering, the method of recrystallizing is dissolving by heating and precipitating by cooling;

and/or, when the post-treatment of step 2 comprises cooling and filtering and further comprises drying and recrystallizing sequentially and immediately after filtering, or recrystallizing without drying directly after filtering, the solvent used for the recrystallizing is a $C_1$-$C_4$ alcohol;

and/or, when the post-treatment of step 2 comprises cooling and filtering and further comprises drying and recrystallizing sequentially and immediately after filtering, or recrystallizing without drying directly after filtering, the mass ratio of the solvent used for the recrystallizing to the compound of formula 4 is (5 to 15):1.

10. The process of claim 9, wherein when step 2 is carried out in the absence of the acid and the solvent is a mixed solvent of a $C_1$-$C_4$ alcohol and water, the mixed solvent of a $C_1$-$C_4$ alcohol and water is a mixed solvent of methanol and water with a mass ratio of 3:1;

and/or, the temperature of step 2 is 60° C. to 65° C.;

and/or, when the post-treatment of step 2 comprises cooling and filtering and further comprises drying and recrystallizing sequentially and immediately after filtering, or recrystallizing without drying directly after filtering and the method of recrystallizing is dissolving by heating and precipitating by cooling, the temperature for dissolving is 50° C. to 70° C.;

and/or, when the post-treatment of step 2 comprises cooling and filtering and further comprises drying and recrystallizing sequentially and immediately after filtering, or recrystallizing without drying directly after filtering and the method of recrystallizing is dissolving by heating and precipitating by cooling, the cooling is gradient cooling and the temperature is reduced by 5° C. per 1 h to 1.5 h, the initial temperature of the gradient cooling is 40° C. to 50° C.;

and/or, when the post-treatment of step 2 comprises cooling and filtering and further comprises drying and recrystallizing sequentially and immediately after filtering, or recrystallizing without drying directly after filtering, the solvent used for the recrystallizing is selected from the group consisting of methanol, ethanol and isopropanol;

and/or, when the post-treatment of step 2 comprises cooling and filtering and further comprises drying and recrystallizing sequentially and immediately after filtering, or recrystallizing without drying directly after filtering, the mass ratio of the solvent used for the recrystallizing to the compound of formula 4 is (5 to 10):1.

11. The process of claim 6, wherein step 2 is carried out in the presence of an acid.

12. The process of claim 6, wherein the compound of formula 3 is prepared by a process comprising step 1: reacting a compound of formula 1:

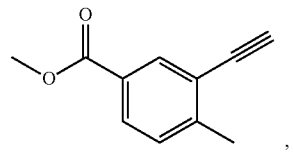

with a compound of formula 2:

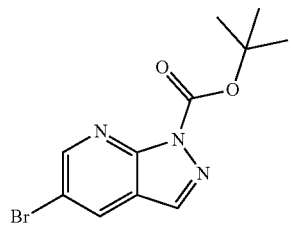

in a solvent and in the presence of a base, a palladium catalyst and a catalyst ligand that is a copper compound and/or triphenylphosphine.

13. The process of claim 12, wherein step 1 is carried out under the protection of nitrogen or inert gas;

and/or, in step 1, the solvent comprises N-methylpyrrolidone, DMSO, DMF, N,N-dimethylacetamide, acetonitrile, toluene, dioxane or THF;

and/or, in step 1, the volume/mass ratio of the solvent to the compound of formula 2 is (5 to 10) mL:1 g;

and/or, in step 1, the molar ratio of the catalyst to the compound of formula 2 is (0.01 to 0.05):1;

and/or, in step 1, the molar ratio of the catalyst ligand to the catalyst is (0.8 to 1.2):1;

and/or, in step 1, the base is an organic base and/or an inorganic base;

and/or, in step 1, the molar ratio of the base to the compound of formula 2 is (1.0 to 1.5):1;

and/or, in step 1, the molar ratio of the compound of formula 1 to the compound of formula 2 is (0.95 to 2.0):1;

and/or, the reaction temperature of step 1 is 40° C. to 80° C.;

and/or, the post-treatment of step 1 comprises mixing with water and filtering.

14. The process of claim 13, wherein in step 1, the solvent is N-methylpyrrolidone, DMSO, DMF, N,N-dimethylacetamide or acetonitrile;

and/or, in step 1, the volume/mass ratio of the solvent to the compound of formula 2 is (7 to 10) mL:1 g;

and/or, in step 1, the palladium catalyst is selected from the group consisting of $PdCl_2(PPh_3)_2$, $Pd(dppf)_2Cl_2$, $Pd(OAc)_2$ and palladium carbon;

and/or, in step 1, the molar ratio of the catalyst to the compound of formula 2 is (0.01 to 0.03):1;

and/or, in step 1, when the catalyst ligand includes a copper compound, the copper compound is selected from the group consisting of CuI, CuBr, $Cu_2O$, CuO and Cupric acetate;

and/or, in step 1, the molar ratio of the catalyst ligand to the catalyst is 1:1;

and/or, in step 1, when the base includes an organic base, the organic base comprises pyridine, an alkali metal salt of a $C_1$-$C_4$ alcohol, or —N($R^4$)($R^5$)($R^6$), wherein each of $R^4$, $R^5$ and $R^6$ independently represents hydrogen or a $C_1$-$C_4$ alkyl;

and/or, in step 1, when the base includes an inorganic base, the inorganic base is an alkali metal carbonate and/or an alkali metal hydroxide;

and/or, in step 1, the molar ratio of the base to the compound of formula 2 is (1.2 to 1.3):1;

and/or, in step 1, the molar ratio of the compound of formula 1 to the compound of formula 2 is (1.2 to 1.5):1;

and/or, the reaction temperature of step 1 is 60° C. to 75° C.;

and/or, when the post-treatment of step 1 comprises mixing with water and filtering, it further comprises mixing with an amino acid compound before mixing with water;

and/or, when the post-treatment of step 1 comprises mixing with water and filtering, the mixing temperature in the mixing with water step is 20° C. to 25° C.;

and/or, when the post-treatment of step 1 comprises mixing with water and filtering, the filtering further comprises washing with water;

and/or, when the post-treatment of step 1 comprises mixing with water and filtering, it further comprises slurrying after filtering.

15. The process of claim 14, wherein in step 1, the solvent is N-methylpyrrolidone, DMSO, DMF or N, N-dimethylacetamide;

and/or, in step 1, the palladium catalyst is $PdCl_2(PPh_3)_2$ or $Pd(dppf)_2Cl_2$;

and/or, in step 1, when the catalyst ligand includes a copper compound, the copper compound is CuI or CuBr;

and/or, in step 1, when the base includes an organic base and the organic base includes an alkali metal salt of a $C_1$-$C_4$ alcohol, the alkali metal salt of the $C_1$-$C_4$ alcohol is potassium tert-butoxide and/or sodium tert-butoxide;

and/or, in step 1, when the base includes an organic base and the organic base includes or —N($R^4$)($R^5$)($R^6$), the —N($R^4$)($R^5$)($R6^3$) comprises $Et_3N$, DIPEA, (i-Pr)$_2$NH or $Bu_3N$;

and/or, in step 1, when the base includes an inorganic base and the inorganic base includes an alkali metal carbonate, the alkali metal carbonate is $K_2CO_3$ and/or $Cs_2CO_3$;

and/or, in step 1, when the base includes an inorganic base, the inorganic base includes an alkali metal hydroxide, the alkali metal hydroxide is NaOH and/or KOH;

and/or, in step 1, the molar ratio of the compound of formula 1 to the compound of formula 2 is (1.2 to 1.3):1;

and/or, the reaction temperature in step 1 is 65° C. to 70° C.;

and/or, when the post-treatment of step 1 comprises mixing with water and filtering and further comprises mixing with an amino acid compound before mixing with water, the amino acid compound is selected from the group consisting of cysteine, N-acetyl-L-cysteine, ethylenediaminetetraacetic acid, sodium edetate and dithiocarbamates;

and/or, when the post-treatment of step 1 comprises mixing with water and filtering and further comprises mixing with an amino acid compound before mixing with water, the molar ratio of the amino acid compound to the compound of formula 2 is (0.1 to 0.5):1;

and/or, when the post-treatment of step 1 comprises mixing with water and filtering and further comprises mixing with an amino acid compound before mixing with water, the mixing temperature upon mixing with an amino acid compound is 35° C. to 45° C.;

and/or, when the post-treatment of step 1 comprises mixing with water and filtering and further comprises mixing with an amino acid compound before mixing with water, the mixing time for mixing with an amino acid compound is 4 h to 5 h;

and/or, when the post-treatment of step 1 comprises mixing with water, filtering and further comprises slurrying immediately after filtering, the solvent used for slurrying is a mixed solvent of ethyl acetate and n-heptane with a volume ratio of 1:1;

and/or, when the post-treatment of step 1 comprises mixing with water, filtering and further comprises slurrying immediately after filtering, the volume/mass ratio of the solvent to the crude filter cake used for slurrying is (5 to 7) mL:1 g.

16. A process for preparing a compound of formula 4:

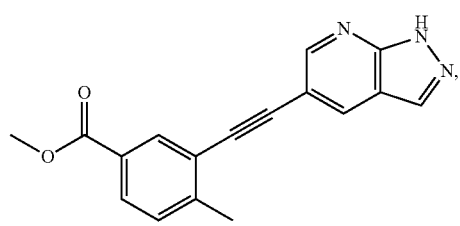

comprising step 2: converting a compound of formula 3:

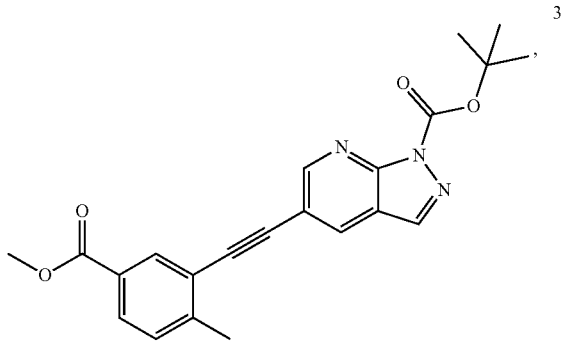 [SMILES: COC(=O)c1ccc(C)c(C#Cc2cnc3c(cnn3C(=O)OC(C)(C)C)c2)c1]

to the compound of formula 4 in a solvent, and wherein:

(i) step 2 is carried out in the absence of the acid, the solvent is acetonitrile, a mixed solvent of acetonitrile and water or a mixed solvent of a $C_1$-$C_4$ alcohol and water; or (ii) step 2 is carried out in the presence of an acid.

17. The process of claim 16, wherein the compound of formula 3 is prepared by a process comprising step 1: reacting a compound of formula 1:

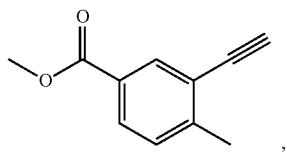

with a compound of formula 2:

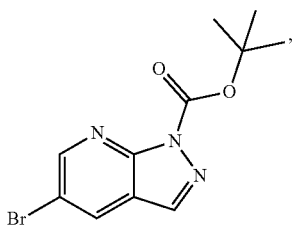

in a solvent and in the presence of a base, a palladium catalyst and a catalyst ligand that is a copper compound and/or triphenylphosphine.

18. A process for preparing a compound of formula 3:

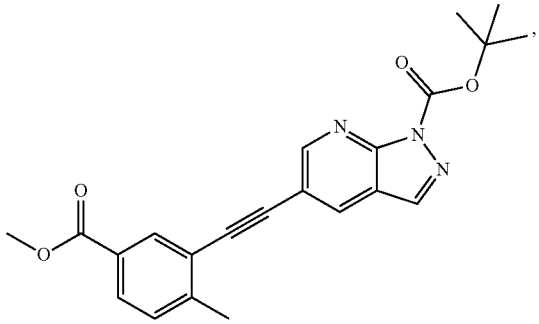

comprising step 1: reacting a compound of formula 1:

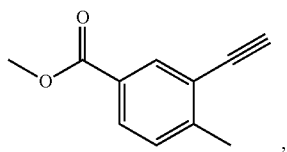

with a compound of formula 2:

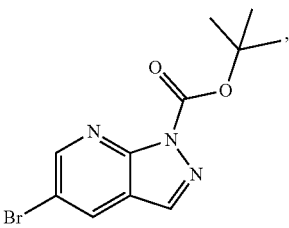

in a solvent and in the presence of a base, a palladium catalyst and a catalyst ligand that is a copper compound and/or triphenylphosphine.

19. A compound of formula 3 or a compound of formula 4,

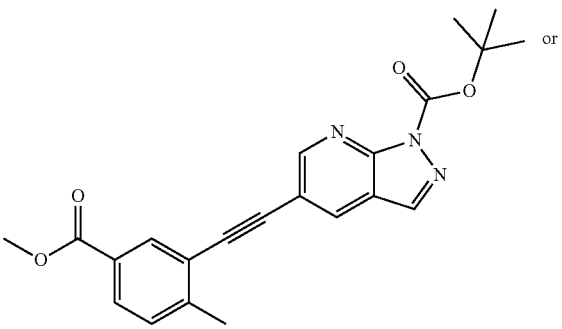

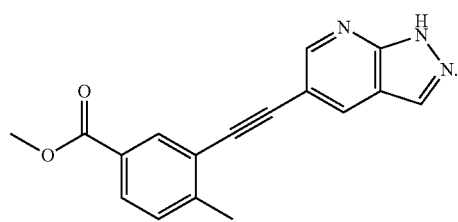

* * * * *